United States Patent [19]
Amiji

[11] Patent Number: 5,904,927
[45] Date of Patent: May 18, 1999

[54] DRUG DELIVERY USING PH-SENSITIVE SEMI-INTERPENETRATING NETWORK HYDROGELS

[75] Inventor: Mansoor M. Amiji, Attleboro, Mass.

[73] Assignee: Northeastern University, Boston, Mass.

[21] Appl. No.: 08/818,973

[22] Filed: Mar. 14, 1997

[51] Int. Cl.⁶ ........................................................ A61F 13/00
[52] U.S. Cl. ............................ 424/422; 424/443; 424/489
[58] Field of Search .................................... 424/422, 443, 424/489

[56] References Cited

U.S. PATENT DOCUMENTS 4,933,182  6/1990  Higashi et al. ........................... 424/435
5,306,550  4/1994  Nishiyama et al. ...................... 428/288

OTHER PUBLICATIONS

Amiji, "Permeability and Blood Compatibility Properties of Chitosan–Poly (ethylene oxide) Blend Membranes for Haemodialysis", Biomaterials, 16:593–599, 1995.

Patel et al., "pH–Sensitive Swelling and Drug–Release Properties of Chitosan–Poly (ethylene oxide) Semi–interpenetrating Polymer Netword", Hydrogels and Biodegradable Polymers for Bioapplications pp. 209–220, 1996.

Patel et al., "Preparation and Characterization of Freeze–dried Chitosan–Poly (ethylene oxide) Hydrogels for Site–Specific Antibiotic Delivery in the Stomach", Pharmaceutical Research, 13:588–593, 1996.

Primary Examiner—D. Gabrielle Brouillette
Attorney, Agent, or Firm—Weingarten, Schurgin, Gagnebin & Hayes LLP

[57] ABSTRACT

Drug-delivery devices and methods of their use are disclosed, which devices consist of at least a semi-interpenetrating network (semi-IPN) hydrogel comprising a first, cationic polymer such as chitosan and a second high molecular weight neutral polymer such as polyethylene oxide, the semi-IPN having been freeze-dried after formation of the semi-IPN, and a drug composition. A therapeutic method of treating gastric disease is also disclosed comprising the step(s) of introducing to a gastric area to be treated a drug-delivery device according to the disclosure, whereupon the device releases the drug or therapeutic agent contained in the device. The hydrogels of the disclosure are advantageously used for site-specific drug delivery in the gastro-intestinal tract where there is a range of pH from 1.0 to 1.5 in the stomach to about 7.5 in the small intestine.

12 Claims, 11 Drawing Sheets

_US 5,904,927_

DRUG DELIVERY USING PH-SENSITIVE SEMI-INTERPENETRATING NETWORK HYDROGELS

CROSS REFERENCE TO RELATED APPLICATIONS

None

STATEMENT REGARDING FEDERALLY SPONSORED RESEARCH OR DEVELOPMENT

None

BACKGROUND OF THE INVENTION

Hydrogels are three dimensional polymeric networks that can swell and retain a significant fraction, e.g., more than 20% of water within its structure, but do not dissolve. Hydrogels are well-suited for use as a base material for biologically active molecules, and have distinct advantages in these type of systems. Small molecules such as drugs can diffuse through hydrogels. Their rate of permeation can be controlled by designing the hydrogel to be specific for the intended end use. Compared to more hydrophobic materials, hydrogels have weaker interactions with molecules immobilized onto or within them. This leaves a large portion of these molecules to be active. Enzymes, for instance, when immobilized in hydrogels retain a significant fraction of their bioactivity. Hydrogels show good biocompatibility with blood and tissue, giving them an extended residence period within the tissue, making the hydrogel devices useful for long-term treatment of various conditions. Biomolecules such as enzymes can also be immobilized for later release on the large number of polar reactive sites in the hydrogel.

Biologically active molecules which may be entrapped or immobilized in hydrogels include antibiotics, drug antagonists, antibodies, estrous inducers, anticoagulants, anticancer drugs, anti-bacterial agents, enzymes, and pesticides/herbicides.

Peptic-ulcer disease (PUD) is a heterogeneous group of chronic and recurrent disorders of the alimentary mucosa, usually involving the stomach and the proximal portion of the duodenum. Gastric ulcer (GU) and duodenal ulcer (DU) are the two most common forms of PUD. The role of *Helicobacter pylori* in the pathogenesis of PUD has been extensively investigated. *H. pylon* has been strongly associated with about 80% of patients with GU and up to 100% of patients with DU. It is also associated with 85% of the patients with gastritis. *H. pylon* is localized in the gastric mucosa; as such, localized release of drug is desired. Certain factors govern the efficiency of the local action. For example, certain antibacterial agents, e.g., penicillin and erythromycin, are degraded by acidic pH, possibly necessitating the case of acid-stable antibiotics to avoid the chances of local drug inactivation in the stomach. Gastric residence time of locally acting agents also plays an important role. Bismuth complexes, for example, have shown better action as compared to other drugs used against *H. pylon*. These compounds deposit on the external surface and beneath the cell wall of the organism, not only increasing the gastric residence time but also the concentration at the site of action.

SUMMARY OF THE INVENTION

A drug-delivery device is disclosed, which consists of at least a semi-interpenetrating network (semi-IPN) hydrogel comprising a first, cationic polymer such as chitosan and a second high molecular weight neutral polymer such as polyethylene oxide, which has been freeze-dried after formation of the semi-IPN, and a drug composition. A therapeutic method of treating gastric disease is also disclosed comprising the step(s) of introducing to a gastric area to be treated a drug-delivery device according to the disclosure, whereupon the device releases the drug or therapeutic agent contained in the device.

BRIEF DESCRIPTION OF THE DRAWINGS

The invention will be more fully understood by reference to the following Detailed Description Of The Invention in conjunction with the following Drawings, of which.

DETAILED DESCRIPTION OF THE INVENTION

Figure 1:
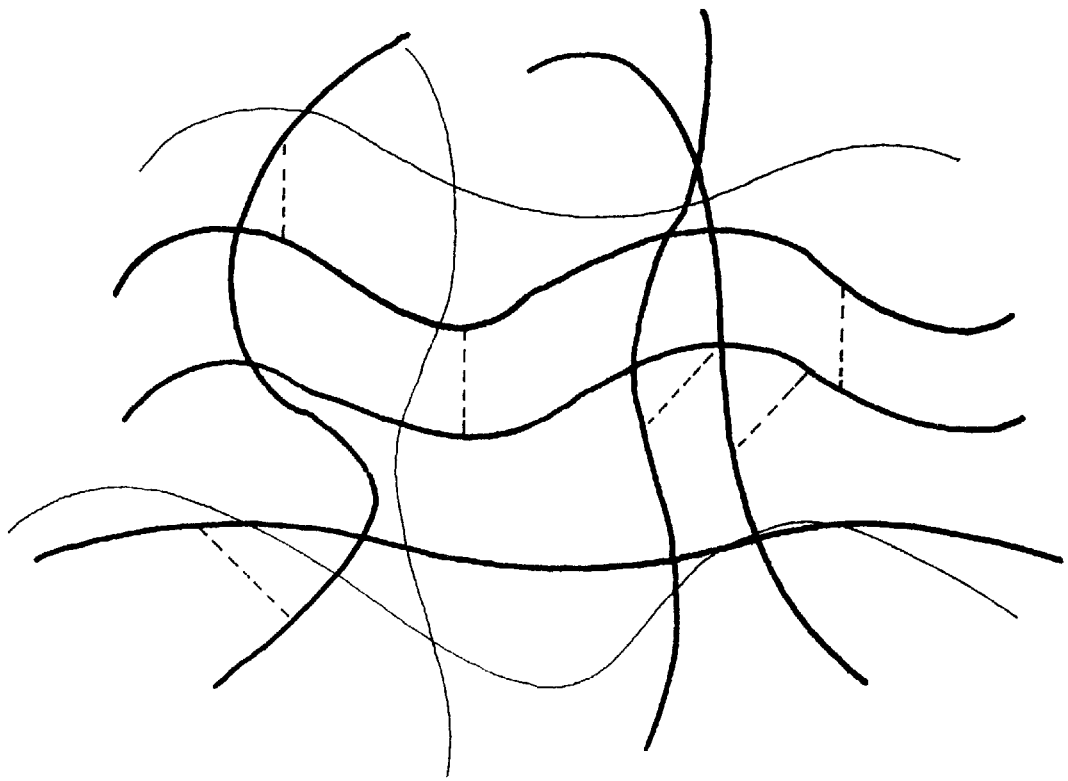
FIG. 1 depicts a semi-IPN in simplified form.

An interpenetrating polymer network (IPN) is defined herein as a combination of two or more polymers to form a network, at least one of which is polymerized and/or crosslinked in the immediate presence of the other. A semi-IPN, as illustrated in simplified form in FIG. 1, results when at least one of the polymers is crosslinked. Crosslinking may be via covalent or ionic bonds.

Semi-IPN hydrogels in accordance with the disclosure may be synthesized in two general ways. In the sequential method, the water-soluble monomer, initiator, and crosslinking agents are mixed to form a first (crosslinked) polymer hydrogel. A second (uncrosslinked) polymer is then formed within the first (crosslinked) polymer hydrogel. The resulting semi-IPN is thus formed in situ. In the simultaneous method, the first water-soluble monomer and crosslinking agent are combined with the second monomer, and both of these polymers are synthesized together using the same initiator by independent, non-interfering reactions. An advantage of the simultaneous method over the sequential method is the ease of processing. For example, the two components can be pre-polymerized and mixed; crosslinking agent(s) can then be added and mixed. This mixture can then be poured into molds and allowed to gel to the required form. The final product can be made into a variety of useful configurations, such as round discs, films, fibers, powders, and microparticulates, e.g., microspheres and nanospheres.

Crosslinking agents for use in the present invention include chemical compounds which react with amine or hydroxyl groups of the first (crosslinked) polymer hydrogel, e.g., chitosan. Such compounds include dialdehydes (e.g., glyoxal and glutaraldehyde); dicarboxylic acids and salts thereof; diisocyanates; epichlorohydrin; and benzoquinone. Since the crosslinking may also be ionic in nature crosslinking may be also promoted through the use of agents such as salts containing divalent or trivalent anions, such as sulfates, phosphates and tripolyphosphates.

Semi-IPN hydrogels in accordance with the disclosure may be loaded with drugs using any method that provides for the desired concentration of the drug in the hydrogel without interfering with the advantageous properties of either the drug or the hydrogel. One such method involves mixing the drug with the polymer blend to obtain a uniform distribution of the drug before the crosslinking agent is added ("gelling"). A second method involves swelling of the pre-formed hydrogels in a solution of the drug. The second method is preferred if the drug is soluble enough to enter the swollen hydrogel, or is or may be unstable during the gelling process. In this method, the swollen hydrogel will entrap the drug.

After gelling the hydrogels may be cut to a desired size and may also be neutralized with base, e.g., 0.1 M NaOH, followed by washing with de-ionized distilled water.

After the gelling process the hydrogel is dried, preferably by freeze-drying. It has been found that freeze-dried hydrogels in accordance with the disclosure are particularly advantageous in that upon swelling at low pH, they swell particularly rapidly to quickly enable the drug contained in the hydrogel matrix to diffuse out and be delivered to the target. This is particularly important when considering use of hydrogels in the gastrointestinal tract for drug delivery. Gastric emptying time is typically about 30 min to 1.5 h; as such, fast swelling and drug release, preferably within the first 30 minutes of swelling in SGF, is highly important in ensuring that the treatment method is successful. It is theorized that the significantly larger pore size of the freeze-dried hydrogels of the disclosure, i.e., about 8–10 μm, appears to contribute to faster rate of swelling, as the swelling medium can be absorbed by capillary action. The increase in the rate of swelling of the hydrogel would correspondingly increase the rate of outflux of entrapped drug in these systems. It should be noted that theory offered only as a possible explanation of the advantages of the present disclosure, and is not intended to limit the invention claimed herein.

The process of hydrogel swelling in aqueous medium involves three primary forces: 1) the free energy of mixing of the network chains with the solvent; 2) the osmotic force, responsible for the swelling, works outward; and 3) the elastic force, responsible for the maintaining the structure of the hydrogel, works inward. The osmotic force and the elastic force work in opposite directions with respect to each other. At a certain time point (equilibrium) in swelling, the respective magnitude of these two forces becomes equal and the hydrogel cannot swell any more. The osmotic force is due to the binding of counterions onto the charged functional group of the polymer and therefore is dependent on the charge density of the polymer. The elastic force results from the crosslinking of two or more polymer chains. The crosslinking density determines the magnitude of the elastic forces; the higher the crosslinking density, lower will be the total swelling.

In a semi-IPN hydrogel of the disclosure which contains a water soluble drug, the drug is immobilized in the hydrogel matrix during manufacture. Swelling leads to transformation of the semi-IPN hydrogel from a glassy form to a more rubbery form; as the polymer swells in water, the drug begins to diffuse out. Thus, drug release depends on two simultaneous rate processes, water migration into the device and drug diffusion outward through the swollen gel matrix.

The pH-sensitive semi-IPN hydrogels disclosed herein comprise first cationic polymers having ionizable functional groups such as —$NH_2$, and which ionize at low pH, i.e., pH values such as found in the gastrointestinal tract, e.g., from 1 to about 4. The cationic polymers may be natural or synthetic in origin. Cationic polymers which may be used in the disclosed hydrogels include chitosan; cationic cellulose derivatives such as UCARE® (Union Carbide); and cationic polyacrylates such as Eudragit® (Rohm and Haas) and poly(dimethylaminoethyl methacrylate).

Chitosan (poly[(1-4) 2-amino-2-deoxy-β-D-glucan]) is a cationic polymer which is an N-deacetyl derivative of chitin. The glucosamine content is about 90% of the polymer structure. Chitosan is a linear cationic polyelectrolyte with high charge density; each glucosamine unit, with a $PK_a$ of 6.4 to 7.0, has at least one positive charge. Being non-toxic, biodegradable, and a natural polymer, chitosan has good biocompatibility; it has also been found to have anti-ulcer properties, making it a particularly good choice for use in treating gastric diseases. At low pH, chitosan becomes viscous and cohesive and binds with anionic polymers such as mucin in the gastrointestinal tract. The amino groups (—$NH_2$) become protonated (—$NH_3^+$) at acidic pH. As stated before, at low pH the semi-IPNs of the disclosure swell due to the repulsion of the protonated (—$NH_3^+$) groups, allowing the semi-IPN to release the drug.

The second high molecular weight neutral polymer has a molecular weight of at least 100,000 daltons and is advantageously between 100,000 and $8 \times 10^6$ daltons, preferably between $1 \times 10^6$ and $2.5 \times 10^6$ daltons (viscosity average molecular weight $M_v$). The second high molecular neutral polymer allows the hydrogel to swell quickly to enable drug diffusion to the target. Such polymers which may be used are, e.g., polyalkylene oxides and copolymers thereof such as poly(ethylene oxide) (PEO) [or poly(ethylene glycol) (PEG)]; polyalkylene oxide copolymers, e.g., diblock and triblock copolymers, of PEO and poly(propylene oxide) (PPO); poly(vinylpyrrolidone) (PVP) and copolymers thereof; poly(vinylalcohol) (PVA) and copolymers thereof such as PVA-poly(vinylacetate) copolymer; celluloses such as methylcellullose and hydroxypropylcellulose; dextran; and gelatin. It has been found that increased content and molecular weight of the second high molecular weight neutral polymer in the semi-IPN hydrogel increases the swelling ability of the hydrogel in simulated gastric fluid (SIF).

Therapeutic medications that may be entrapped or immobilized in the semi-IPN hydrogels disclosed herein for localizing the medication in the gastric area include antibiotics effective against *H. pylon* such as penicillins, macrolides, imidizoles, and tetracyclines; agents that decrease and/or inhibit acid secretion in the stomach such as antacids, histamine H-2 receptor antagonists, and proton pump inhibitors; mucosal protective agents such as sucralfate and prostaglandin derivatives; anti-cancer agents; and vaccines.

EXAMPLES

To illustrate the efficacy of the disclosed semi-IPN hydrogels as drug delivery devices, chitosan-PEO semi-IPN hydrogels were made as follows. Chitosan (Sea-Cure®-210) was obtained from Pronova Biopolymers, (Raymond, Wash.). The molecular weight of chitosan was $1.0 \times 10^6$ daltons and the degree of deacetylation was greater than 80%. Poly(ethylene oxide) (PEO) was purchased from Sigma Chemicals Co., (St. Louis, Mo.) or obtained from Union Carbide, (Danbury, Conn.). Glyoxal was purchased from Aldrich Chemical Company Inc., (Milwaukee, Wis.). Amoxicillin and metronidazole were purchased from Sigma Chemicals Co., (St. Louis, Mo.).

Chitosan-PEO hydrogels herein were prepared as follows. Chitosan and PEO were dissolved in 0.1 M acetic acid to obtain 2% (w/v) solutions of each. These solutions were filtered through glass wool before use. The crosslinking agent glyoxal, was also dissolved in 0.1 M acetic acid. The concentration of the crosslinking agent in the final hydrogel was 8.0 mg/ml. The hydrogels were synthesized as semi-IPN using the simultaneous method: the two polymer solutions were mixed to form a 40 ml homogenous blend. The crosslinking agent was dissolved in 0.1 M acetic acid to give a volume of 10 ml. This solution was then added to the polymer blend and mixed thoroughly, to obtain a final volume of 50 ml for the hydrogel. The blend was then poured into a petri dish and allowed to gel at room temperature. After the hydrogels were formed they were cut into discs of approximately 20 mm diameter. The discs were neutralized in 0.1 M NaOH, followed by extensive washing with deionized distilled water.

The hydrogel discs were then dried. Comparison air dried hydrogels were dried at room temperature to a constant weight. Freeze-dried hydrogel discs were rapidly frozen at about –70° C. while swollen, in dry ice-acetone mixture. They were then immediately transferred to freeze-drying containers, which were then attached to a Freeze Mobile 5SL (The Virtis Co., Inc., Gardiner, N.Y.) freeze drier. These hydrogel discs were allowed to dry overnight at –57° C. with a vacuum (103 millitorr) applied to the container. All control hydrogels herein were prepared with chitosan alone.

I. Experimental Procedures

A. Swelling Studies

The swelling of different hydrogels can be compared using their swelling ratios. Swelling ratio can be calculated by the following formula:

$$Q = W^*/W$$

where Q is the swelling ratio, $W^*$ is the weight of the swollen hydrogel and W is the weight of the dry hydrogel. The dried hydrogels were swollen in 50 ml of swelling medium, at 37° C. At different time points, the hydrogels were removed from the swelling mediums and were blotted to remove surface moisture using a piece of Kimwipe® tissue (Kimberly-Clark, Roswell, Ga.). Their weights were measured and the hydrogels were immediately returned to the swelling medium. Swelling ratio (Q) was then calculated from the weights of the swollen and dry hydrogels.

B. Swelling Media

Swelling media used to test swelling in different pH ranges encountered in the gastro-intestinal tract were simulated gastric fluid (SGF) and simulated intestinal fluid (SIF). SGF and SIF were prepared by the protocol described in USP XXII.

The composition of SGF and SIF were as follows:

Simulated Gastric Fluid (SGF)
Sodium chloride 2.0 g
Concentrated HCl 7.0 ml
Water to volume 1000 ml
This test solution has a pH of about 1.2.
Simulated Intestinal Fluid (SIF)
Monobasic potassium phosphate 6.8 g
Sodium hydroxide (0.2 N) 190 ml
Water to volume 1000 ml C. Effect of Chitosan:PEO Ratio and PEO Molecular Weight Two groups of hydrogels were prepared to study the effects of the component ratio of the semi-IPN on swelling. The first set contained hydrogels made with different chitosan:PEO ratios. The chitosan:PEO (weight) ratios were 90:10; 80:20; and 70:30. PEO having a molecular weight of 1,000,000 daltons was used.

The second set contained hydrogels having varying molecular weights of PEO, but a constant chitosan:PEO ratio. The molecular weights were 10,000; 20,000; 100,000; 600,000; and 1,000,000 daltons. The chitosan:PEO ratio was 80:20 percent. Both sets of hydrogels were subjected to dynamic swelling studies as detailed below.

D. Dynamic Swelling Studies

Dynamic hydrogel swelling was studied as follows. The hydrogels were swollen in SGF. Hydrogel weight was measured at time intervals of 5, 10, 15, 20, 25, 30, 40, 50, 60 min, 2, 4, 6, 8, 10, and 24 hours. The swelling ratios were then calculated and compared with that of the control hydrogel (chitosan).

E. pH-Dependent Swelling Studies pH-dependent swelling studies on a preferred composition (chitosan:PEO, 80:20; PEO molecular weight, $1 \times 10^6$ daltons) were conducted as follows. Hydrogels were swollen in 50 ml of SGF or SIF, maintained at 37° C. Hydrogel weight was measured at time intervals of 5, 10, 15, 20, 25, 30, 40, 50, 60 min, 2, 4, 6, 8, 10, 24 hours. The swelling ratios at these time intervals were calculated and compared with that of the control. The swelling at the two different pH values was also compared.

F. Sequential Swelling Studies

Sequential swelling studies to test the swelling behavior of a preferred composition (chitosan:PEO, 80:20; PEO molecular weight, $1 \times 10^6$ daltons) were conducted as follows. Chitosan:PEO and control hydrogels were sequentially swollen, first in SGF, then in SIF. Hydrogels were first swollen in SGF for up to 6 hours and then transferred to SIF for an additional 6 hours. The weight measurements were taken at time intervals of 5, 10, 15, 20, 25, 30, 40, 50, 60 mins, 2, 4, 6 h, in each of these fluids. The swelling ratios at these time intervals were calculated and compared with that of the control hydrogel, which was also subjected to similar sequential swelling studies.

G. Drug Loading and In Vitro Release Studies

Drug-loaded hydrogels were prepared as follows. The desired amount of drug was added to the polymer blend and mixed thoroughly to obtain a uniform distribution of the drug. The crosslinking agent was then added and mixed. The resulting mixture was then allowed to gel, washed as above, and dried (air drying or freeze-drying). Three drugs were studied to test the release properties: riboflavin, amoxicillin, and metronidazole. The hydrogel composition used was:

Chitosan:PEO ratio—80:20

PEO molecular weight—1,000,000 daltons

Crosslinking agent concentration—8.0 mg/ml.

Three sets of drug loaded hydrogels were prepared to test the release under different conditions. A first set of hydrogels were subjected to release studies in SGF and SIF in a stationary bath. To study the effect of shaking, to simulate gastrointestinal movements on drug release, we subjected another set of hydrogels to release studies in a shaker bath at 65 rpm. All sets included control (chitosan) hydrogels, for comparison.

Drug release was tested in 50 ml of SGF and SIF at 37° C. At specified time intervals 1 ml aliquot from each sample was removed and assayed for the drug with a UV160U spectrophotometer (Shimadzu, Columbia, Md.). Sampling intervals for air-dried hydrogels were 5, 10, 15, 20, 25, 30, 40, 50, 60 minutes, 2, 4, 6, 8, 10 and 24 hours. Freeze-dried hydrogels were sampled at 5, 10, 15, 20, 25, 30, 40, 50, 60, 70, 80, 90, 100, 110, 120, 130, 140 and 150 minutes. Riboflavin was measured at 445 nm, amoxicillin at 230 nm, and metronidazole at 276 nm. The samples were replaced immediately after the measurements. The amount of drug released from the hydrogels was calculated from a previously determined standard curve. The release kinetics was described according to the equation developed by Peppas:

$$\frac{M_t}{M\infty} = kt^n,$$

where $M_t$ is the amount of drug released at time t, $M\infty$ is the total amount of drug released, k is a release constant, and n is the release exponent.

The value of n determines the relationship between the rate and time.

H. Scanning Electron Microscopy

To characterize and compare the structure of freeze-dried and air-dried hydrogels, scanning electron microscopy (SEM) was done on samples of these hydrogels. The freeze-dried and air-dried samples were mounted on a specimen mount and coated with gold-palladium. The morphology of chitosan and chitosan-PEO hydrogels were examined at an original magnification of 100 using an AMR-1000 scanning electron microscope (Amray Instruments, Bedford, Mass.) at a working distance of 10 mm and an accelerating voltage of 5.0 kv. During these characterization, we examined the top and the cross-sectional view of the hydrogels. The pore sizes of the freeze-dried and the air-dried hydrogels were then compared.

I. Swelling Studies With Freeze-Dried And Air-Dried Hydrogels

To demonstrate the superiority of freeze-dried hydrogels of the disclosure compared to air dried hydrogels in the area of rate of swelling and drug release in the gastric environment, freeze-dried and air-dried hydrogels were subjected to swelling studies in pepsin-free SGF and pancreatin-free SIF maintained at 37° C. These gels reached equilibrium earlier than air-dried gels. For this reason the time points for measurements were changed as follows: 5, 10, 15, 20, 25, 30, 40, 50, 60, 70, 80, 90, 100, 110, 120, 130, 140 and 150 mins. Control hydrogels were also subjected to similar studies and the swelling kinetics were compared.

II. Experimental Results

A. Effect of Chitosan:PEO Ratio and PEO Molecular Weight

Figure 2:
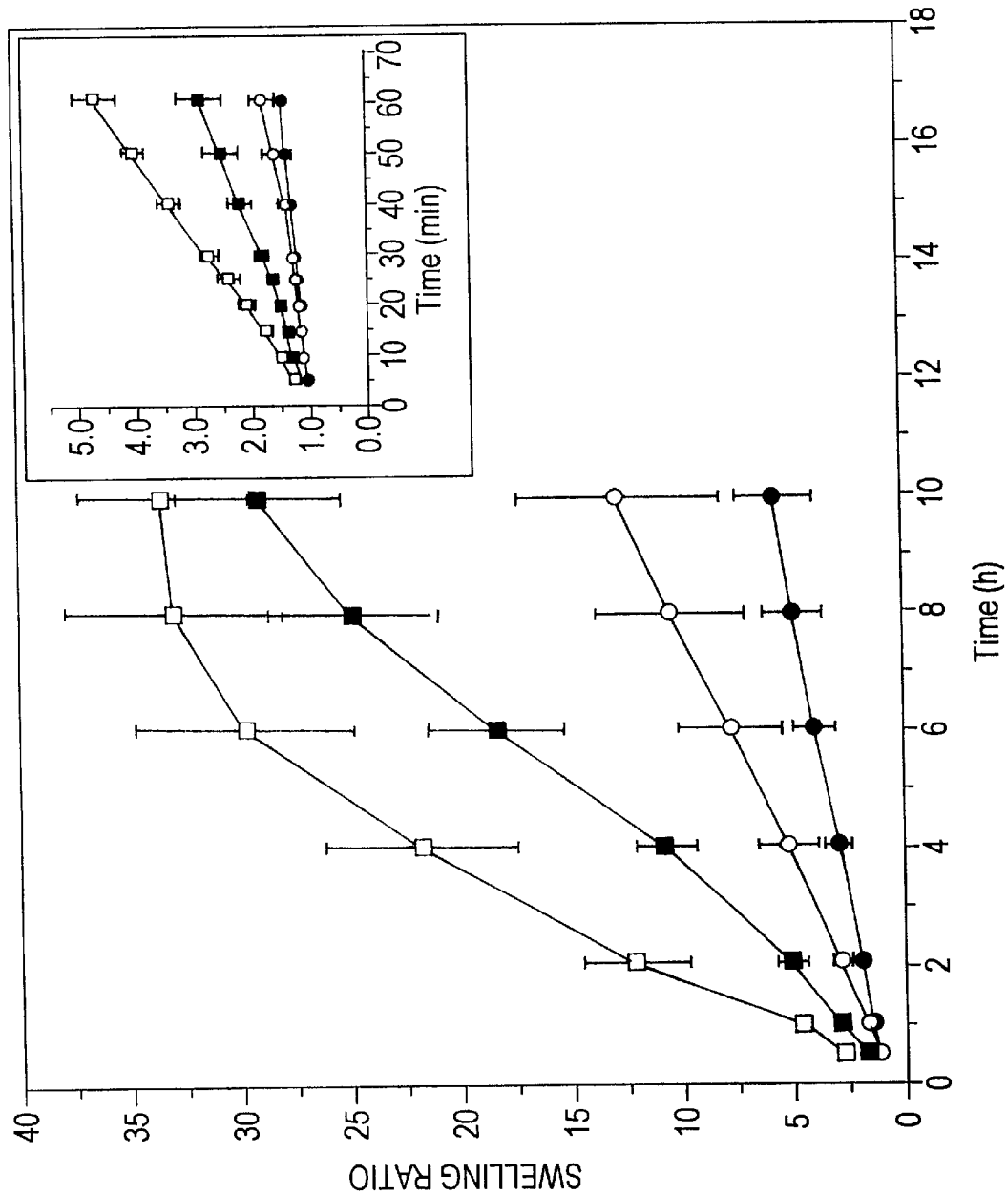
FIG. 2 is a graph showing dynamic swelling of chitosan hydrogels and chitosan-PEO semi-IPN at 37° C. in simulated gastric fluid. The symbols represent chitosan (●), chitosan-PEO (90:10) (○), chitosan-PEO (80:20) (■) and chitosan-PEO (70:30) (□). Each point represents mean ±S.D. (n=4).
Figure 3:
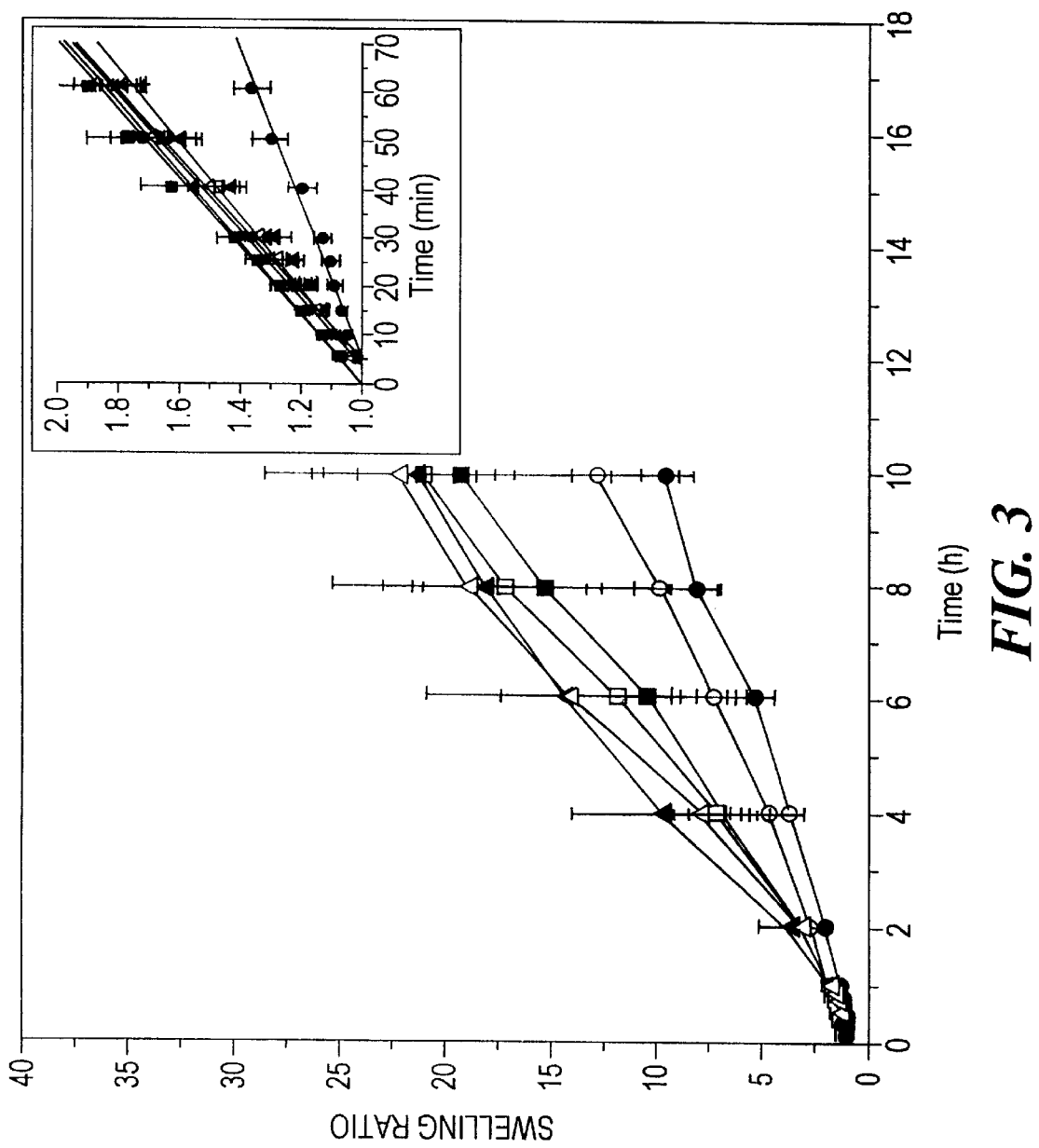
FIG. 3 is a graph showing dynamic swelling of chitosan hydrogels and chitosan-PEO semi-IPN at 37° C. in simulated gastric fluid. The symbols represent chitosan (●), chitosan-PEO (weight ratio of 80:20) hydrogels prepared with PEO of molecular weight 10,000 (○), 20,000 (■), 100,000 (■), 600,000 (▲) and 100,000 (△) daltons. Each point represents means ±S.D. (n=4).

The effect of various chitosan:PEO ratios on the swelling of the semi-IPN is shown in FIG. 2. With an increase in the PEO content there is a marked increase in the swelling ratios. After six hours of swelling, the swelling ratios of chitosan hydrogels, chitosan-PEO (90:10), (80:20), and (70:30) semi-IPN were 3.97, 7.74, 18.39, and 29.81, respectively. The chitosan-PEO (90:10) semi-IPN had swollen by almost twice as much as chitosan hydrogels, while chitosan-PEO (80:20) and (70:30) semi-IPN had swollen five times and eight times higher, respectively. Chitosan-PEO semi-IPN had swollen extensively compared to chitosan hydrogels. The effect of PEO molecular weight on the swelling of the semi-IPN is shown in FIG. 3, which compares the kinetics of the swelling ratios of chitosan hydrogel and chitosan-PEO semi-IPN containing PEO with different molecular weights in simulated gastric fluid at 37° C. At initial time points, the swelling ratios of chitosan-PEO semi-IPN with increasing molecular weight of PEO were not very different. As the duration of swelling continued, however, the swelling ratios of the semi-IPN increased with increasing molecular weight of incorporated PEO. After 6 h of swelling in SGF, the chitosan hydrogel had a swelling ratio of 5.30. The swelling ratio of chitosan-PEO semi-IPN after 6 h, on the other hand, was 11.9 for PEO 100,000 daltons and 14.3 for PEO 1,000,000 daltons. Addition of high molecular weight PEO contributed significantly to the initial swelling of the hydrogels.

B. pH-Dependent Swelling Studies

Figure 4:
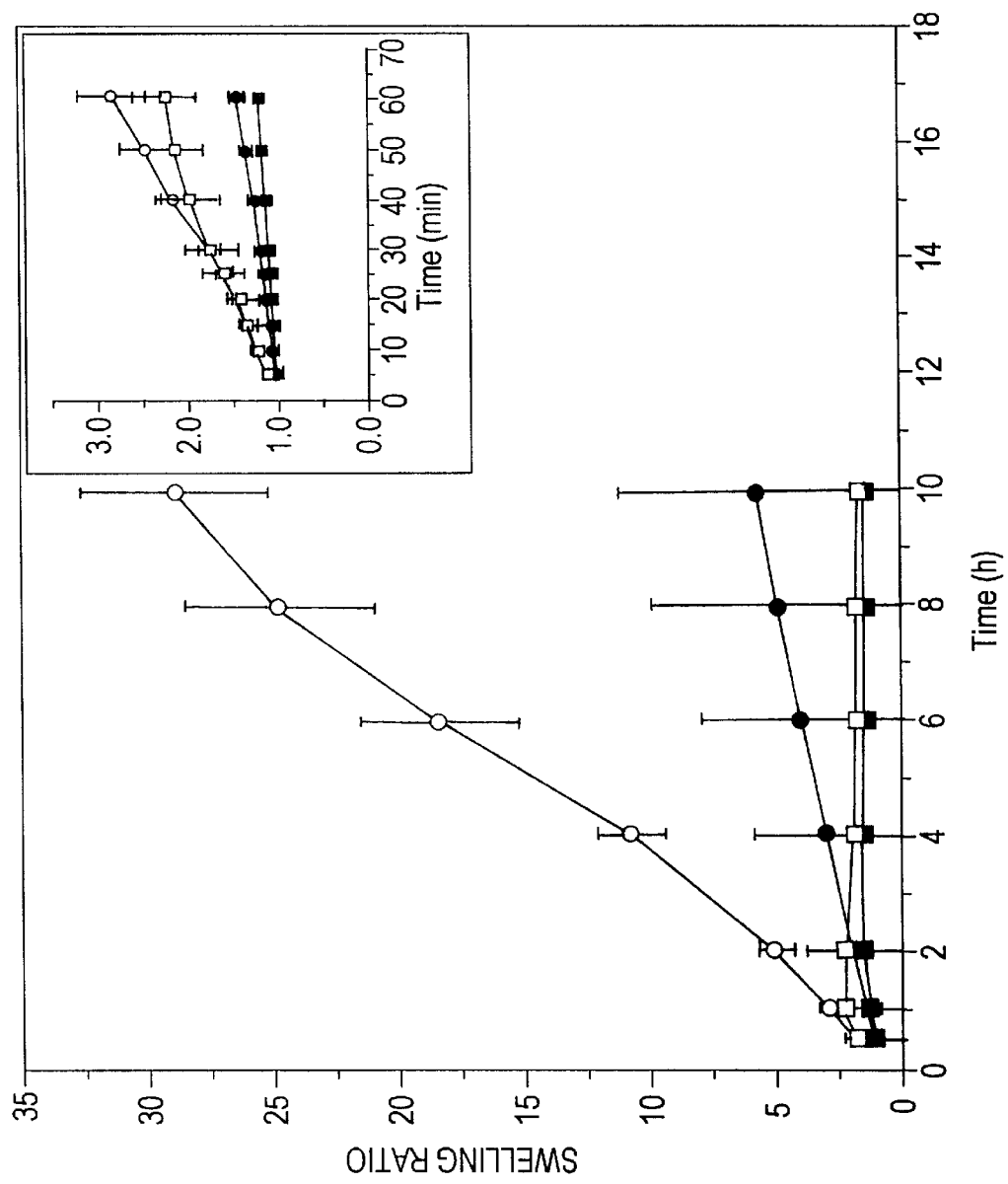
FIG. 4 is a graph showing swelling kinetics of chitosan hydrogels and chitosan-PEO semi-IPN at 37° C. in simulated gastric and intestinal fluids. The symbols represent chitosan (●) and chitosan-PEO (○) in gastric fluid and chitosan (■) and chitosan-PEO (□) in intestinal fluid. Each point represents mean ±S.D. (n=4).

FIG. 4 shows the swelling kinetics of chitosan hydrogels and chitosan-PEO semi-IPN in simulated gastric and intestinal fluid. The swelling ratios of chitosan hydrogels and chitosan-PEO semi-IPN, in the gastric fluid, after 2 hours was 1.95 and 5.03, respectively. After 6 hours of swelling in gastric fluid chitosan-PEO semi-IPN had swollen five times more than control, chitosan hydrogels. The swelling ratios of chitosan and chitosan-PEO semi-IPN in intestinal fluid, after 2 hours was 1.49 and 2.16, respectively. The incorporation of PEO into the network had a less profound effect on the swelling of the hydrogels in the simulated intestinal fluid. These results show that the swelling of chitosan-PEO semi-IPN is not only pH-sensitive, but also that their swelling could be controlled by changing the proportion of the two polymers.

C. Sequential Swelling Studies

Figure 5:
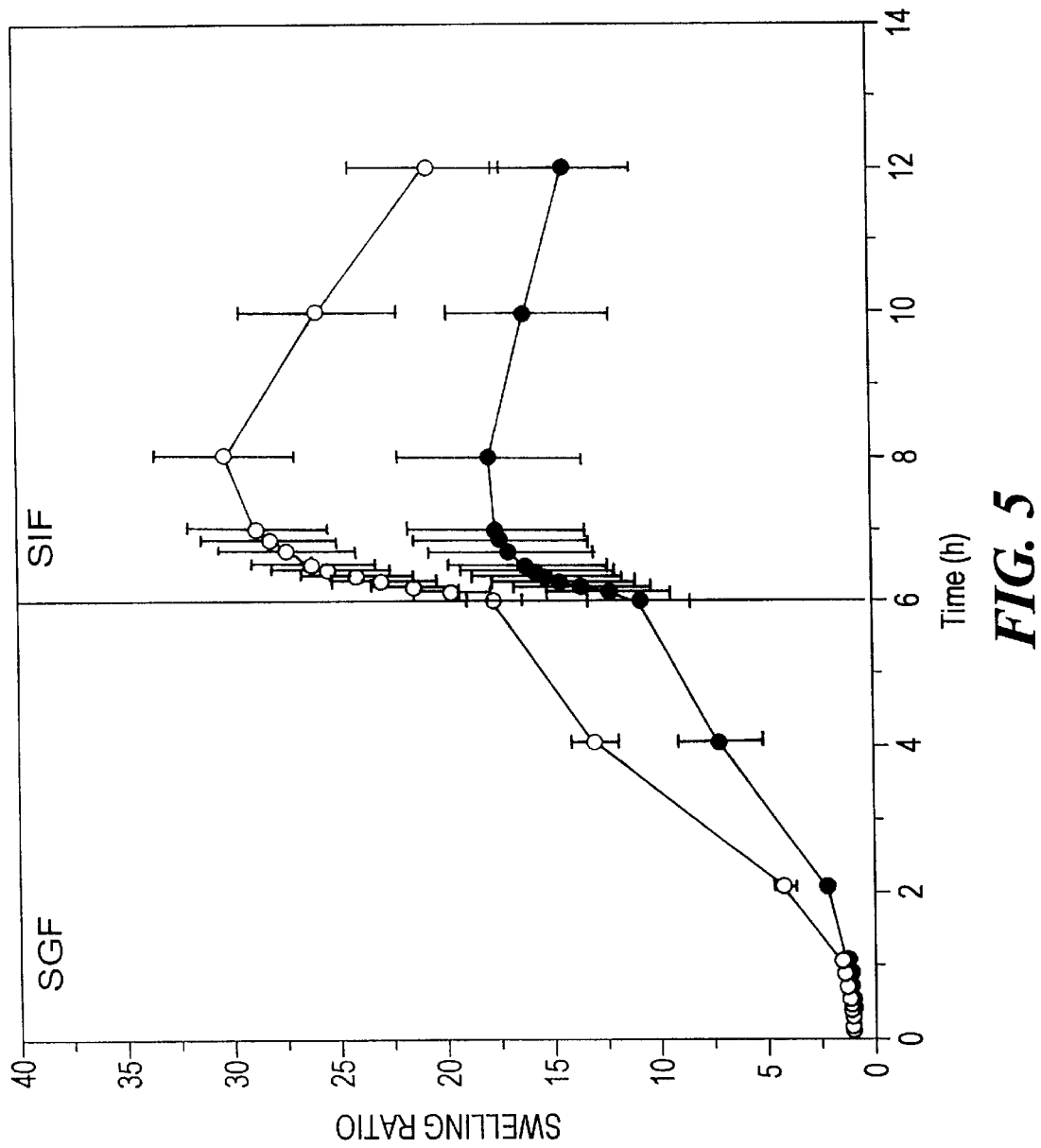
FIG. 5 is a graph showing swelling kinetics of chitosan hydrogels and chitosan-PEO semi-IPN at 37° C. in simulated gastric fluid for first 6 h and intestinal fluid for the next 6 h. The symbols represent chitosan (●) and chitosan-PEO (○) in gastric fluid. Each point represents mean ±S.D. (n=4).

As shown in FIG. 5, the swelling ratio of both the chitosan hydrogel and chitosan-PEO semi-IPN increase not only for the first 6 h kept in SGF, as one would expect, but also for another 2 h after transferring the gels to SIF. After the first 6 h in SGF, the swelling ratio of chitosan hydrogel and chitosan-PEO semi-IPN were 11.1 and 17.8, respectively. After transferring to SIF, they continued to swell even in high pH medium. At the end of 2 h in SIF, the swelling ratios of chitosan hydrogel and chitosan-PEO semi-IPN increased to 17.9 and 30.4, respectively. The swelling ratio started to decrease from this time point. The continuation of swelling for about 2 h, after transferring the hydrogels to SIF, suggest that the exchange of hydronium ions from the swollen matrix is a gradual process. At later time points the swelling ratio decreased as the ion concentration inside the matrix decreased substantially.

D. Drug Loading and In Vitro Release Studies: Air-Dried Samples

Figure 6:
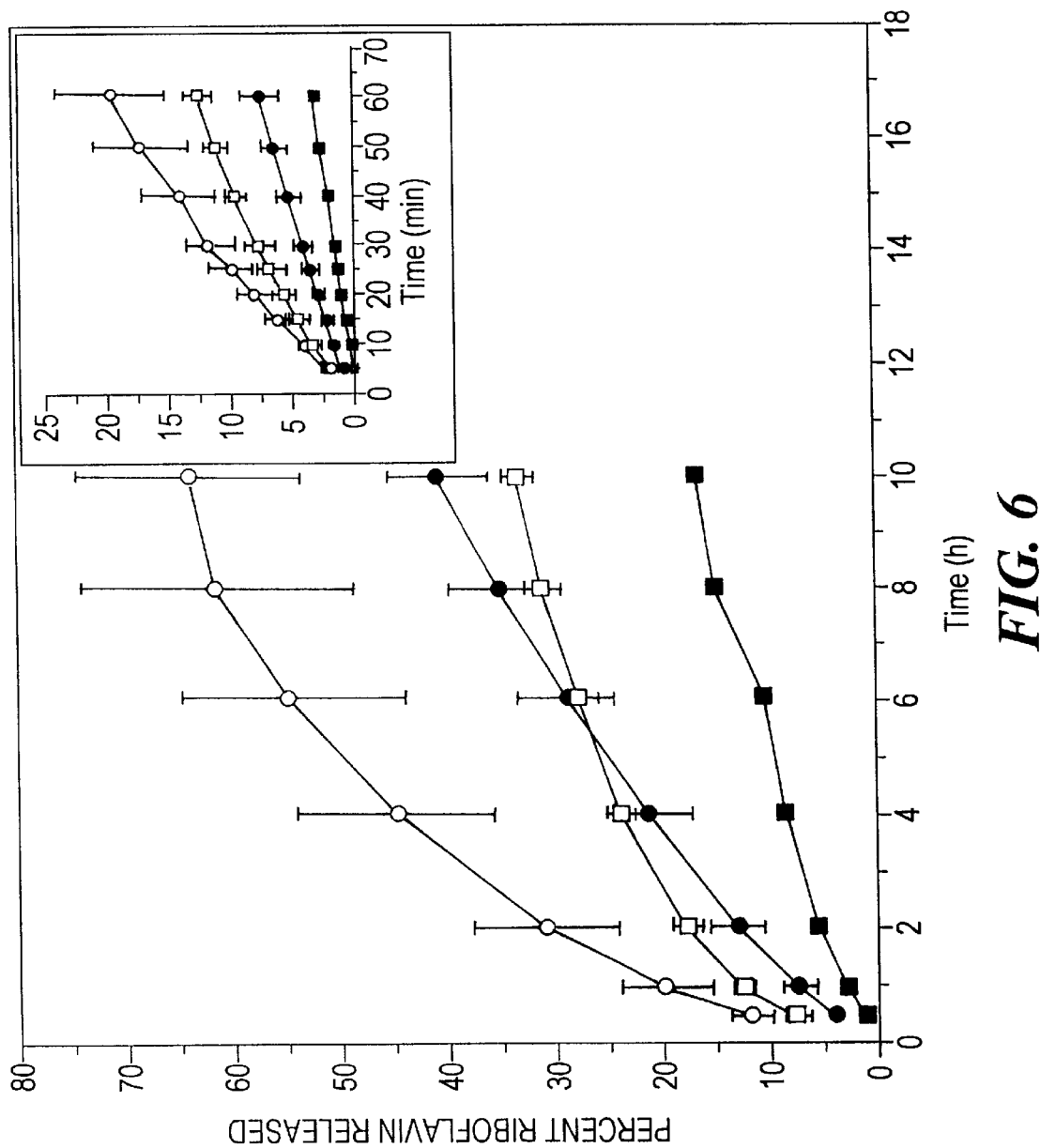
FIG. 6 is a graph showing release of riboflavin from chitosan hydrogels and chitosan-PEO semi-IPN in simulated gastric and intestinal fluids at 37° C. The symbols represent chitosan (●) and chitosan-PEO (○) in gastric fluid and chitosan (■) and chitosan-PEO (□) in intestinal fluid. Each point represents mean ±S.D. (n=4).
Figure 7A:
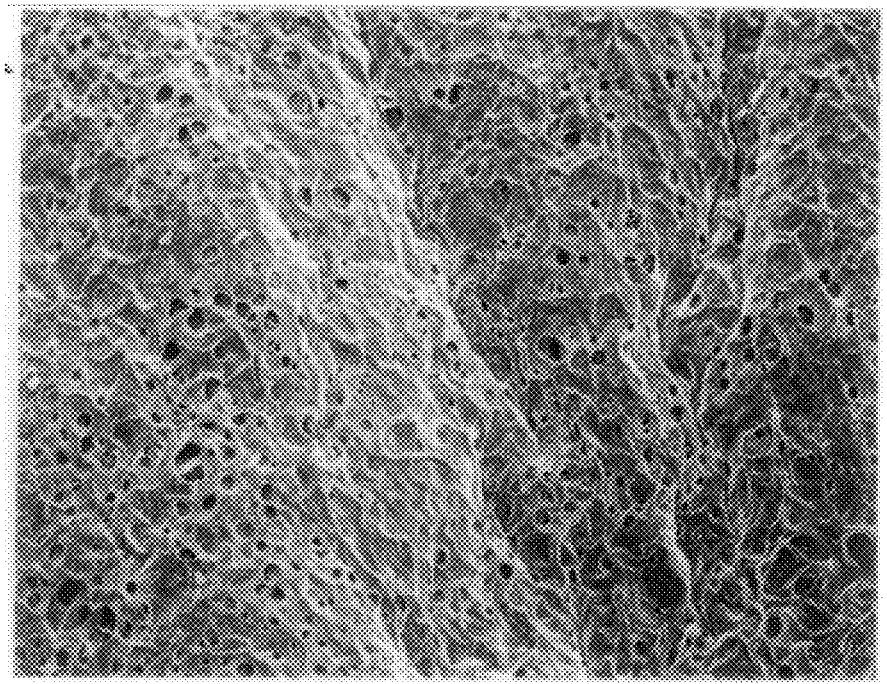
FIGS. 7(a)–7(d) are electron micrographs of freeze dried and air dried semi-IPN hydrogels of the disclosure.
Figure 7B:
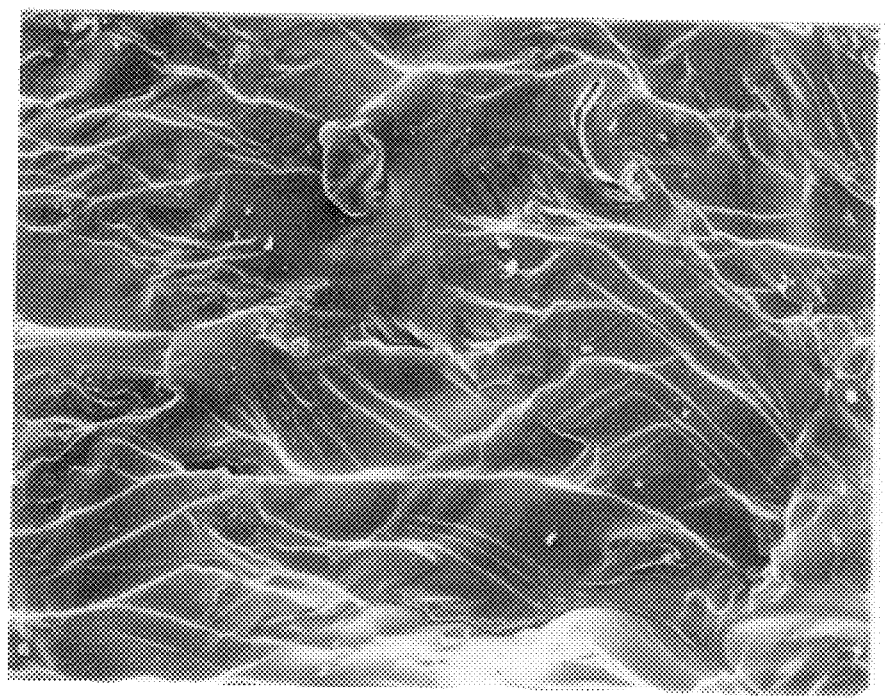
Figure 7C:
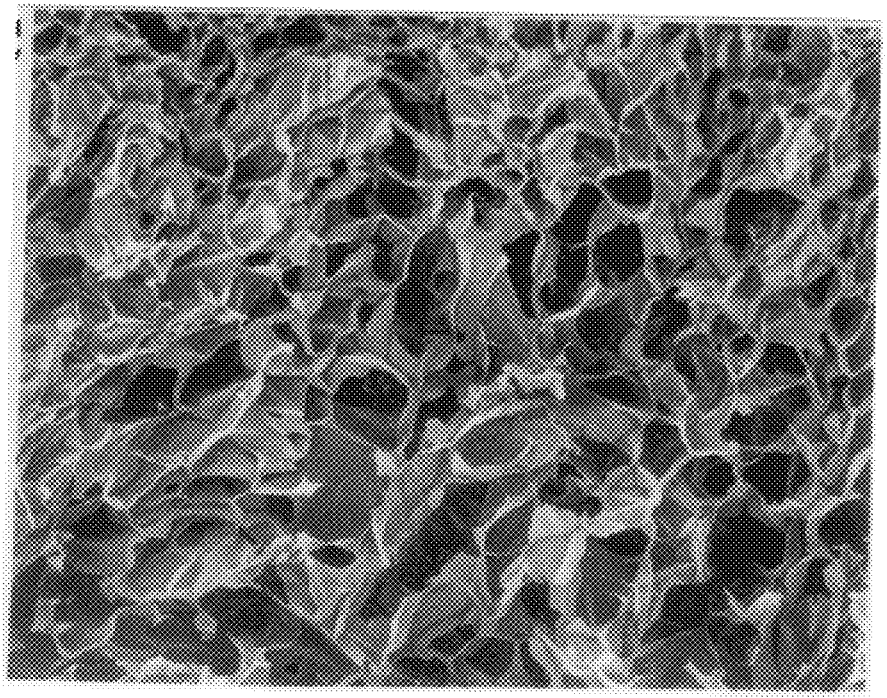
Figure 7D:

FIG. 6 shows the pH-dependent release of riboflavin from chitosan hydrogels and chitosan-PEO semi-IPN. The release exponent (n) for each case was approximately 0.5, regardless of the pH of the medium or the type of hydrogel. After six hours of swelling in simulated gastric fluid, chitosan hydrogels and chitosan-PEO semi-IPN released almost 30% and 55% of the incorporated drug, respectively. On the other hand the release in simulated intestinal fluid after six hours, from chitosan hydrogels and chitosan-PEO semi-IPN was 8.5% and 28% of the incorporated drug, respectively. Addition of PEO to chitosan does significantly change the drug release properties in simulated gastric and intestinal fluids.

E. Comparison of Freeze-Dried and Air-Dried Hydrogels

1) Scanning Electron Microscopy

The results of scanning electron microscopy is shown in FIGS. 7(a)–7(d). The freeze-dried chitosan-PEO semi-IPN surface (FIG. 7(a)) and cross-section (FIG. 7(c)) have much larger pore size compared to the air-dried chitosan-PEO semi-IPN surface (FIG. 7(b)) and cross-section (FIG. 7(d)). The freeze-dried semi-IPN hydrogel pore size ranges from about 8 to 10 $\mu$m.

2) Swelling Behavior of Freeze-Dried and Air-Dried Hydrogels

Figure 8:
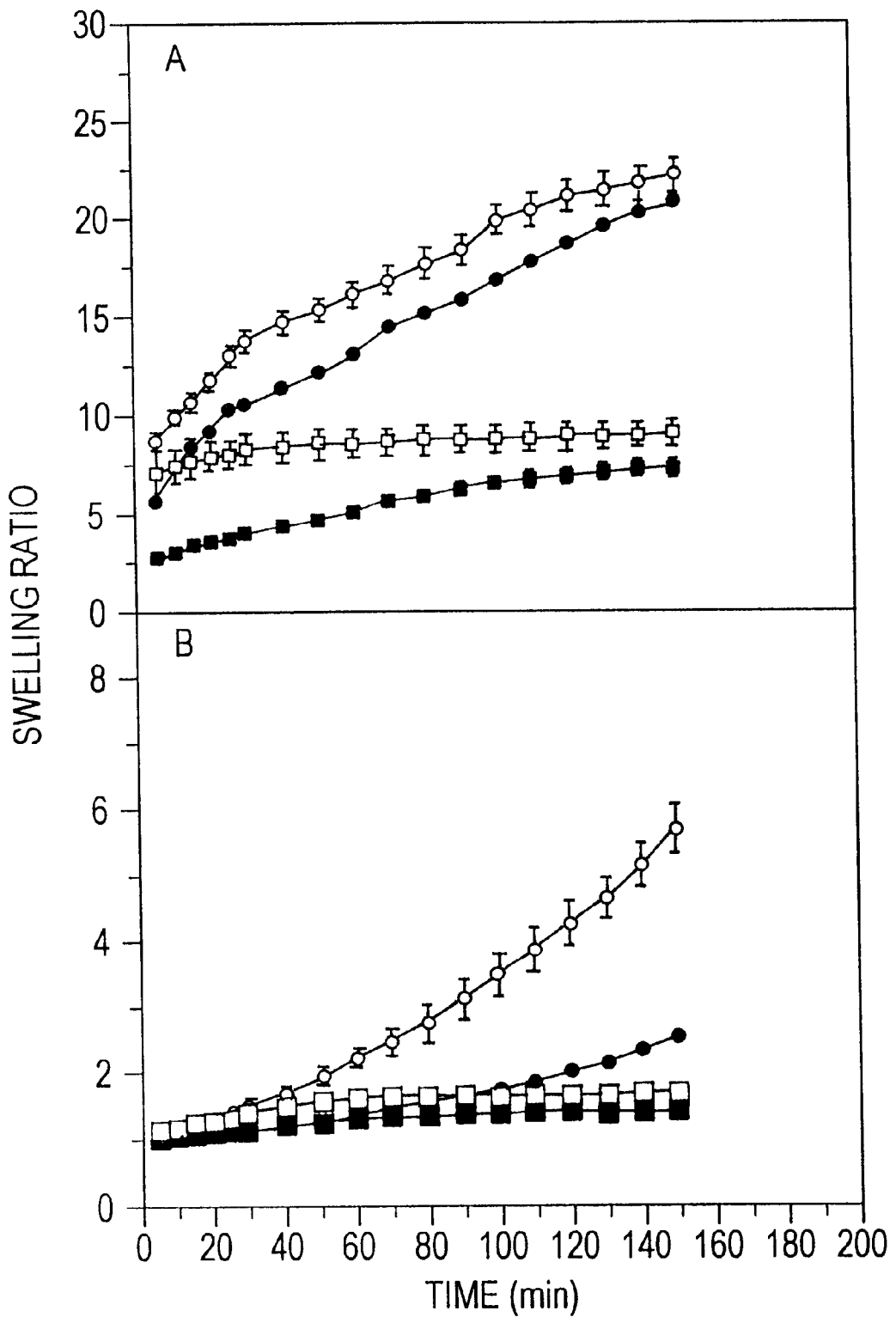
FIG. 8 is a graph showing swelling kinetics of freeze-dried (A) and air-dried (B) chitosan hydrogels and chitosan-PEO semi-IPN at 37° C. in simulated gastric and intestinal fluids. The symbols represent chitosan (●) and chitosan-PEO (○) in gastric fluid and chitosan (■) and chitosan-PEO (□) in intestinal fluid. Each point represents mean ±S.D. (n=4).

The swelling kinetics of freeze-dried and air-dried hydrogels, in simulated gastric and intestinal fluid, are shown in FIGS. 8(A) and (B), respectively. The first point to be noticed is that the swelling ratios of freeze-dried chitosan hydrogels and chitosan-PEO semi-IPN, in SGF or SIF, rises at a much faster rate than the air-dried hydrogels. The swelling of freeze-dried systems reach equilibrium at an early time point. For instance, after 1 h of swelling in SGF, the freeze-dried chitosan hydrogels and chitosan-PEO semi-IPN had a swelling ratio of 13.13 and 16.10, respectively. In contrast, the swelling ratios of air-dried chitosan hydrogels and chitosan-PEO semi-IPN, after 1 h of swelling in SGF, were only 1.37 and 2.26, respectively. The second point to be noticed is that these hydrogels swell much more in SGF as compared to SIF, showing that freeze-drying the gels in itself does not affect the pH-sensitivity of the hydrogel. After 1 h of swelling in SIF, the freeze-dried chitosan hydrogel and chitosan-PEO semi-IPN had a swelling ratio of 5.20 and 8.62, respectively, while in SGF they had a swelling ratio of 13.13 and 16.10, respectively.

3) Drug Release From Freeze-Dried and Air-Dried Hydrogels a. Amoxicillin

Figure 9:
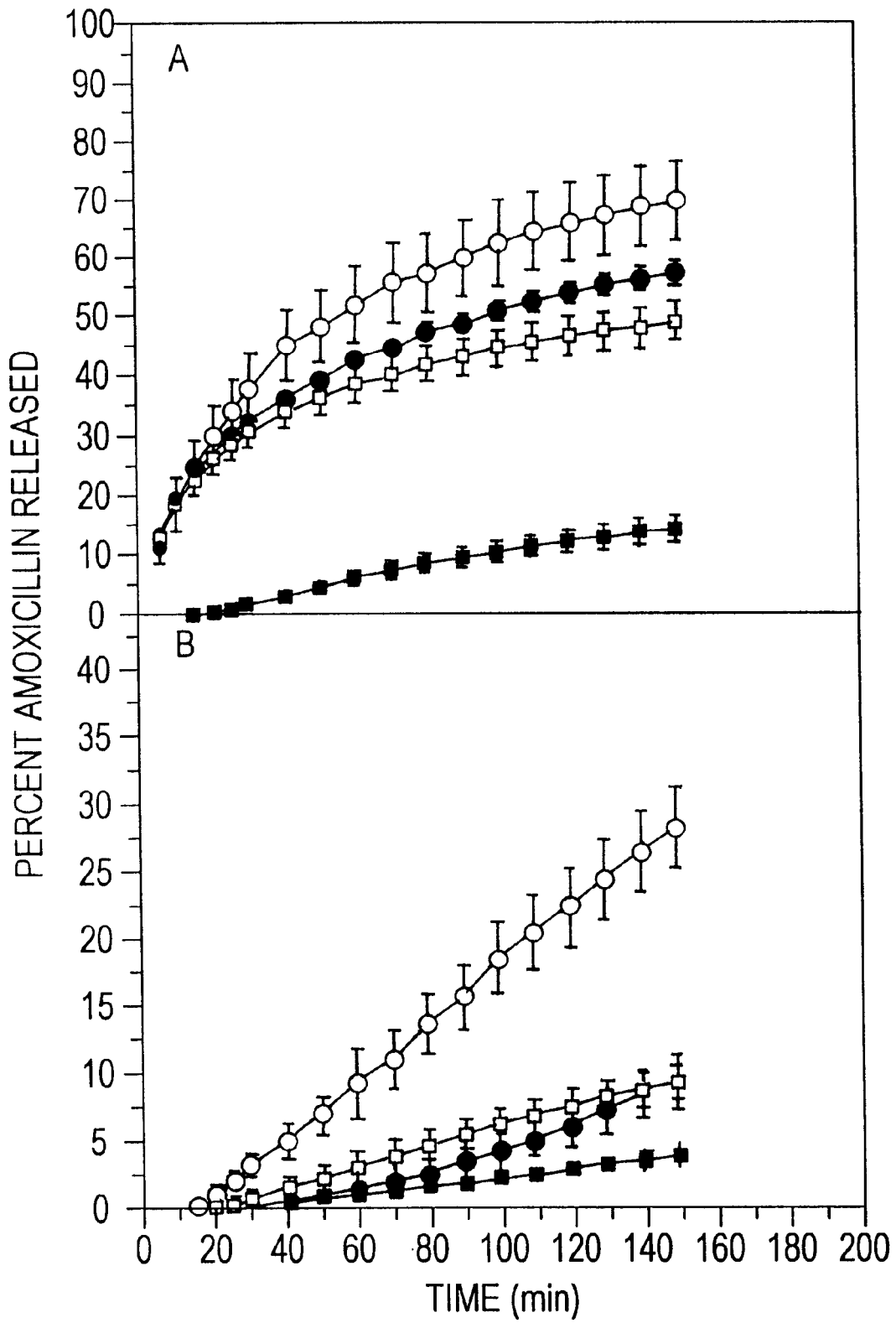
FIG. 9 is a graph showing release of amoxicillin from freeze-dried (A) and air-dried (B) chitosan hydrogels and chitosan-PEO semi-IPN in simulated gastric and intestinal fluids at 37° C. The symbols represent chitosan (●) and chitosan-PEO (○) in gastric fluid and chitosan (■) and chitosan-PEO (□) in intestinal fluid. Each point represents mean ±S.D. (n=4)

The release of amoxicillin in SGF and SIF from freeze-dried and air-dried hydrogels, is shown in FIGS. 9(A) and (B), respectively. After 1 h of swelling in SGF, more than 42.3% and 51.7% of loaded drug was released from freeze-dried chitosan and chitosan-PEO hydrogels, respectively. In contrast, after 1 h of swelling in SGF, only 1.47% and 9.13% of the loaded drug was released from the air-dried chitosan and chitosan-PEO hydrogels, respectively. When comparing the release at pH 1.2 and 7.4, a significantly lower release is observed in SIF compared to SGF. For instance, after 1 h of swelling in SIF, only 6.30% and 38.4% of loaded drug is released from freeze-dried chitosan and chitosan-PEO hydrogels, respectively. These results show that the freeze-dried hydrogels possess the desired properties of pH-sensitivity, and exhibit a rapid rate of swelling and drug release in the gastric pH.

The exponent value (n) for the release of amoxicillin from freeze-dried chitosan hydrogels and chitosan-PEO semi-IPN in SGF were found to be approximately 0.5, suggesting Fickian diffusion mechanism. The exponent values for the release of amoxicillin from air-dried hydrogels were greater than 1.0. The experiments performed for the release studies were limited to 2.5 h. The air-dried hydrogels had not swollen to equilibrium. Since air-dried hydrogels require 6–10 h for equilibrium swelling and completely releasing the entrapped drug, the results obtained from 2.5 h studies did not represent the actual Moo value for air-dried hydrogels.

b. Metronidazole

Figure 10:
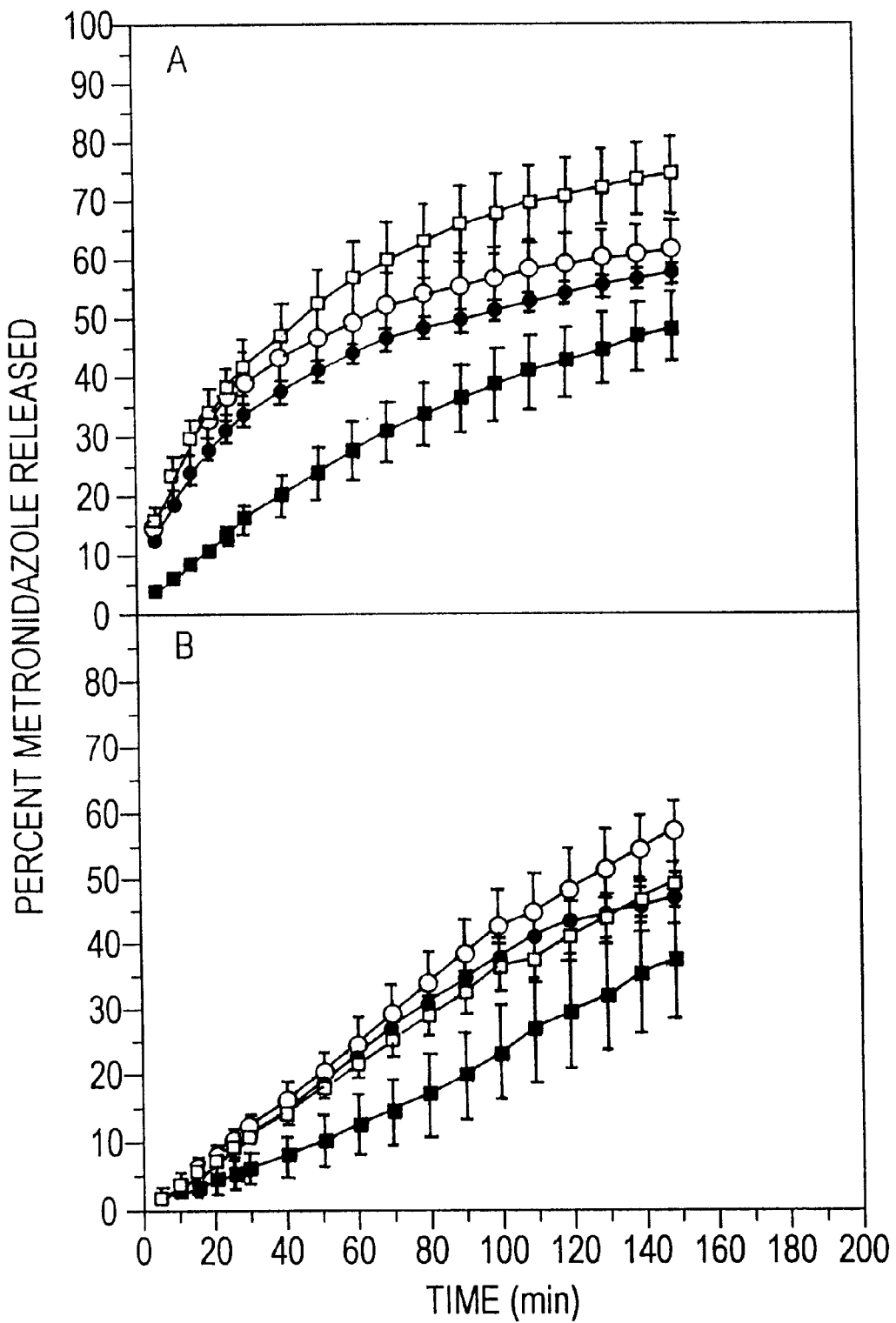
FIG. 10 is a graph showing release of metronidazole from freeze-dried (A) and air-dried (B) chitosan hydrogels and chitosan-PEO semi-IPN in simulated gastric and intestinal fluids at 37° C. The symbols represent chitosan (0) and chitosan-PEO (○) in gastric fluid and chitosan (■) and chitosan-PEO (□) in intestinal fluid. Each point represents mean ±S.D. (n=4).

In addition to the results of release studies done with amoxicillin, we examined the release of the drug metronidazole, from freeze-dried and air-dried systems. FIGS. 10(A) and (B), show the results of metronidazole release in SGF and SIF from freeze-dried and air-dried hydrogels, respectively. These results are comparable to those obtained from the studies with amoxicillin. After 1 h of swelling in SGF about 43.7% and 49.5% of loaded drug was released from freeze-dried chitosan hydrogels and chitosan-PEO semi-IPN, respectively. In contrast, after 1 h of swelling in SGF only 23.05% and 24.72% of the loaded drug was released from air-dried chitosan hydrogels and chitosan-PEO semi-IPN, respectively. Swelling of the chitosan-PEO freeze-dried hydrogels in SIF appears to release more drug compared to release in SGF. For instance, after 1 h of swelling in SIF about 27.4% and 56.6% of loaded drug was released from freeze-dried chitosan and chitosan-PEO hydrogels, respectively. In contrast, the release of metronidazole from chitosan-PEO air-dried hydrogels in SIF was similar to that of riboflavin and amoxicillin. The percent release from air-dried hydrogels was lower in SIF than in SGF. After 1 h of swelling in SIF only 12.6% and 21.5% of loaded drug was released from air-dried chitosan and chitosan-PEO hydrogels, respectively.

The release of metronidazole from the freeze-dried hydrogels in SGF also seem to follow the Fickian diffusion mechanism, as the release exponent (n) value is approximately 0.5. Similar to the release of amoxicillin, the release of metronidazole from air-dried hydrogels have an exponent value near 1.0 since the release studies were limited to 2.5 h.

What is claimed is:

1. A semi-interpenetrating network hydrogel drug-delivery device comprising: a semi-interpenetrating network hydrogel comprising a cationic first polymer and a high molecular-weight, neutral, second polymer having an $M_v$ of at least 100,000 daltons, said semi-interpenetrating network hydrogel having been freeze-dried after formation of said semi-interpenetrating network hydrogel; and a water-soluble drug composition.

2. The drug delivery device of claim 1 wherein said drug is selected from the group consisting of antibiotics; drug antagonists; antibodies; estrous inducers; anticoagulants; anticancer drugs; anti-bacterial agents; enzymes; pesticides/herbicides; antacids; histamine H-2 receptor antagonists; proton pump inhibitors; mucosal protective agents; and vaccines.

3. The drug delivery device of claim 1 wherein said cationic first polymer is selected from the group consisting of chitosan; cationic celluloses; and cationic polyacrylates.

4. The drug delivery device of claim 1 wherein said high molecular weight neutral second polymer is selected from the group consisting of polyalkylene oxides and copolymers thereof.

5. The drug delivery device of claim 4 wherein said polyalkylene oxides and copolymers thereof are selected from the group consisting of poly(ethylene oxide); diblock and triblock copolymers of PEO and poly(propylene oxide); poly(vinylpyrrolidone) and copolymers thereof; poly(vinylalcohol) and copolymers thereof; celluloses; dextran; and gelatin.

6. The drug delivery device of claim 1 wherein the ratio of said first Polymer to said second polymer is from about 90:10 to 70:30.

7. The drug delivery device of claim 1 wherein the $M_v$ of said second polymer is from about 100,000 to $8 \times 10^6$ daltons.

8. The drug delivery device of claim 1 wherein the $M_v$ of said second polymer is from about $1 \times 10^6$ and $2.5 \times 10^6$ daltons.

9. A method of making a drug delivery device, comprising the steps of providing a cationic first polymer;

forming a semi-interpenetrating network hydrogel by combining said cationic first polymer with a high molecular weight neutral second polymer having an $M_v$ of at least 100,000 daltons and crosslinking one of said polymers;

freeze-drying said semi-interpenetrating network hydrogel; and adding a drug composition to said semi-interpenetrating network hydrogel.

10. The method of claim 9 for the comprising the step of adding a drug to said semi-interpenetrating network hydrogel before said freeze-drying step.

11. The method of claim 9 wherein said crosslinking is accomplished by the use of a crosslinking agent selected from the group consisting of glyoxal; glutaraldehyde; dicarboxylic acids and salts thereof; diisocyanates; epichlorohydrin; and benzoquinone.

12. A semi-interpenetrating network hydrogel drug-delivery device comprising chitosan; and a polyethylene oxide having an $M_v$ of from about $1 \times 10^6$ to $2.5 \times 10^6$ daltons, said semi-interpenetrating network network hydrogel having been freeze-dried after formation of said semi-interpenetrating network hydrogel; and a drug composition effective for treating peptic-ulcer diseases.

* * * * *

UNITED STATES PATENT AND TRADEMARK OFFICE
CERTIFICATE OF CORRECTION

PATENT NO : 5,904,927
DATED : May 18, 1999
INVENTOR(S) : Mansoor M. Amiji

It is certified that error appears in the above-identified patent and that said Letters Patent are hereby corrected as shown below:

Column 1, line 46, "pylon", should read --pylori--;

Column 1, line 49, "pylon", should read --pylori--;

Column 1, line 58, "pylon", should read --pylori--;

Column 2, line 66, "(O)", should read --(●)--; and

Column 5, line 22, "pylon", should read --pylori--.

Signed and Sealed this

Twenty-second Day of May, 2001

*Attest:*

NICHOLAS P. GODICI

*Attesting Officer*     *Acting Director of the United States Patent and Trademark Office*